(12) United States Patent
Hwang et al.

(10) Patent No.: US 12,311,041 B2
(45) Date of Patent: May 27, 2025

(54) NANOCAPSULES FORMING EMULSION PARTICLES AND EMULSION COMPOSITION INCLUDING SAME

(71) Applicant: AMOREPACIFIC CORPORATION, Seoul (KR)

(72) Inventors: Yoonkyun Hwang, Yongin-Si (KR); Jihye An, Yongin-Si (KR); Dajeong Lee, Yongin-Si (KR); Youngsun Kim, Yongin-Si (KR); Seunghan Park, Yongin-Si (KR); Byungguen Chae, Yongin-Si (KR); Dongwon Choi, Yongin-Si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 1116 days.

(21) Appl. No.: 17/268,156

(22) PCT Filed: Aug. 28, 2019

(86) PCT No.: PCT/KR2019/011001
§ 371 (c)(1),
(2) Date: Feb. 12, 2021

(87) PCT Pub. No.: WO2020/045983
PCT Pub. Date: Mar. 5, 2020

(65) Prior Publication Data
US 2021/0299008 A1   Sep. 30, 2021

(30) Foreign Application Priority Data

Aug. 31, 2018  (KR) .................. 10-2018-0103955
Aug. 22, 2019  (KR) .................. 10-2019-0102837

(51) Int. Cl.
| | |
|---|---|
| A61K 8/06 | (2006.01) |
| A61K 8/14 | (2006.01) |
| A61K 8/34 | (2006.01) |
| A61K 8/55 | (2006.01) |
| A61K 8/67 | (2006.01) |
| A61K 8/68 | (2006.01) |
| A61K 8/92 | (2006.01) |
| B82Y 5/00 | (2011.01) |
| B82Y 30/00 | (2011.01) |
| B82Y 40/00 | (2011.01) |

(52) U.S. Cl.
CPC .............. *A61K 8/062* (2013.01); *A61K 8/14* (2013.01); *A61K 8/34* (2013.01); *A61K 8/55* (2013.01); *A61K 8/678* (2013.01); *A61K 8/68* (2013.01); *A61K 8/92* (2013.01); *A61K 2800/10* (2013.01); *A61K 2800/21* (2013.01); *A61K 2800/413* (2013.01); *A61K 2800/805* (2013.01); *B82Y 5/00* (2013.01); *B82Y 30/00* (2013.01); *B82Y 40/00* (2013.01)

(58) Field of Classification Search
None
See application file for complete search history.

(56) References Cited

U.S. PATENT DOCUMENTS

| | | |
|---|---|---|
| 5,643,555 A | 7/1997 | Collin et al. |
| 2011/0236447 A1 | 9/2011 | Yoshimura et al. |
| 2013/0115258 A1 | 5/2013 | Singh et al. |
| 2013/0336902 A1 | 12/2013 | Fernandez Prieto et al. |
| 2015/0017306 A1 | 1/2015 | Harada et al. |
| 2017/0065952 A1* | 3/2017 | Spyropoulos .......... A61K 8/375 |
| 2018/0200689 A1 | 7/2018 | Zhao et al. |
| 2019/0281852 A1 | 9/2019 | Hanasaki et al. |
| 2020/0214954 A1 | 7/2020 | Choi et al. |

FOREIGN PATENT DOCUMENTS

| | | |
|---|---|---|
| CN | 1701785 A | 11/2005 |
| CN | 102793628 A | 11/2012 |
| CN | 103251539 A | 8/2013 |
| CN | 109771373 A | 5/2019 |
| CN | 110113949 A | 8/2019 |
| EP | 2832437 A1 | 2/2015 |
| EP | 3 530 264 A1 | 8/2019 |
| EP | 3552495 A1 | 10/2019 |
| EP | 3 636 244 A1 | 4/2020 |
| JP | 2006-239666 A | 9/2006 |
| JP | 4527016 B2 | 8/2010 |
| JP | 2011-241175 A | 12/2011 |
| JP | 2013-082643 A | 5/2013 |
| KR | 10-2004-0084364 A | 10/2004 |
| KR | 10-2005-0055114 A | 6/2005 |
| KR | 10-2006-0061879 A | 6/2006 |

(Continued)

OTHER PUBLICATIONS

Seid Mahdi Jafari, et al., "Phytoparticles for the stabilization of Pickering emulsions in the formulation of novel food colloidal dispersions", Trends in Food Science & Technology, 2020, vol. 98, pp. 117-128 (12 pages total).
Zhen Hu et al., "Surfactant-enhanced cellulose nanocrystal Pickering emulsions", Journal of Colloid and Interface Science, 2015, pp. 139-148, 439.
Kazuo Tajima et al., "Three-phase Emulsification: Emulsion Technology without Use of Conventional Surfactant", J. Soc. Cosmet. Chem. Jpn., 2016, pp. 283-293, vol. 50, No. 4.
International Searching Authority, International Search Report pf PCT/KR2019/011001 dated Dec. 2, 2019.
Office Action issued Oct. 13, 2023 in Chinese Application No. 202180017275.4.
Zeng Haiyan, "Preparation and stabilized Pickering emulsions of chitosan nanoparticles", Engineering Science and Technology, 2015, pp. B014-B259, vol. 1 (4 pages total).

(Continued)

*Primary Examiner* — Celeste A Roney
(74) *Attorney, Agent, or Firm* — Sughrue Mion, PLLC (57) ABSTRACT

Nanocapsules that form emulsion particles and an emulsion composition including the nanocapsules are disclosed. The emulsion composition contains an aqueous phase; an oil phase; and emulsion particles surrounded by a plurality of non-amphiphilic nanocapsules located in the interface between the aqueous phase and the oil phase. The emulsion composition is capable of forming emulsion particles in an oil-in-water-type emulsion composition, without using a surfactant.

12 Claims, 7 Drawing Sheets

(56) References Cited

FOREIGN PATENT DOCUMENTS

| | | |
|---|---|---|
| KR | 10-2007-0042298 A | 4/2007 |
| KR | 10-2007-0089358 A | 8/2007 |
| KR | 10-2011-0097918 A | 8/2011 |
| KR | 10-2014-0041453 A | 4/2014 |
| KR | 10-1547528 B1 | 8/2015 |
| KR | 10-2017-0094345 A | 8/2017 |
| KR | 10-2019-0013006 A | 2/2019 |
| KR | 10-2019-0025740 A | 3/2019 |
| TW | 474822 B | 2/2002 |
| WO | WO-2007100182 A1 * | 9/2007 ............... A61K 8/11 |
| WO | 2013/146387 A1 | 10/2013 |
| WO | 2016/098910 A1 | 6/2016 |
| WO | 2018/105747 A1 | 6/2018 |
| WO | 2019/203717 A1 | 10/2019 |
| WO | 2021/172908 A1 | 9/2021 |

OTHER PUBLICATIONS

International Search Report issued Jun. 28, 2021 in International Application No. PCT/KR2021/002404.
Communication issued Jun. 27, 2023 in Korean Application No. 10-2019-0102837.
Communication issued Feb. 20, 2025 in Korean Application No. 10-2020-0024295.
Communication issued Feb. 24, 2025 in Korean Application No. 10-2020-0024296.
Haji, F. et al. "Application of Pickering emulsions in probiotic encapsulation—A review", Current Research in Food Science, 2022, vol. 5, pp. 1603-1615 (13 pages).
Japanese Office Action dated Mar. 14, 2025 in Application No. 2022-550809.

* cited by examiner

Before application

After application

[Example 11]

[O/W emulsion]

NANOCAPSULES FORMING EMULSION PARTICLES AND EMULSION COMPOSITION INCLUDING SAME

CROSS REFERENCE TO RELATED APPLICATIONS

This application is a National Stage of International Application No. PCT/KR2019/011001 filed on Aug. 28, 2019, claiming priority based on Korean Patent Application No. 10-2018-0103955 filed on Aug. 31, 2018 and Korean Patent Application No. 10-2019-0102837 filed on Aug. 22, 2019.

TECHNICAL FIELD

Disclosed in the present disclosure are nanocapsules forming emulsion particles and an emulsion composition including the same.

BACKGROUND ART

The general emulsification technology uses surfactants. Another well-known representative method controls the physical properties of powder particles, e.g., silica or other powder particles, thereby stabilizing the Janus particles having hydrophilicity and oleophilicity at the same time at the interface. However, this method shows problems in terms of formulation stability associated with freezing and thawing and provides a limited feeling of use with a unique finish feeling due to the intrinsic properties of the powder particles. In addition, there are still many technical obstacles to large-scale production of powders with Janus structure.

The existing emulsification technologies include a technology using a polyoxyethylene hydrogenated castor oil derivative, wherein polyethylene glycol (PEG) is used to confer both hydrophilic and oleophilic properties, thereby ensuring stability at the water-oil interface. However, with increasing concerns about the harmful ingredients of cosmetics, it has been recently reported that PEG induces skin troubles or rashes by stimulating the mucous membranes of skin. Therefore, more and more customers ask for PEG-free cosmetics and the use of PEG in cosmetics is decreasing rapidly.

REFERENCES OF RELATED ART

Patent Documents

KR 10-1547528 B1.

DISCLOSURE

Technical Problem

In an aspect, the present disclosure is directed to providing an emulsion composition wherein water-dispersible non-amphiphilic nanocapsules form emulsion particles without using a surfactant. Whereas a Pickering emulsion, wherein solid particles are used to emulsification, requires modification of physical properties of the solid particles to provide amphiphilicity, the water-dispersible non-amphiphilic nanocapsules according to the present disclosure do not require modification of physical properties and form emulsion particles stably at the water-oil interface.

In another aspect, the present disclosure is directed to providing a method for preparing the emulsion composition.

Technical Solution

In an aspect, the present disclosure provides an emulsion composition including: an aqueous phase; and an oil phase, wherein a plurality of non-amphiphilic nanocapsules are located at the interface between the aqueous phase and the oil phase, and emulsion particles surrounded by the plurality of non-amphiphilic nanocapsules are formed.

In an exemplary embodiment, the emulsion composition may be an oil-in-water type.

In an exemplary embodiment, the emulsion composition may not exhibit oil separation when it is prepared into a dried product by freezing at a temperature of −60° C. or lower, and then sublimating and eliminating water under reduced pressure.

In an exemplary embodiment, the non-amphiphilic nanocapsules may have a particle size of 10 nm to 1 μm on average.

In an exemplary embodiment, the emulsion particles may have a particle size of 1-30 μm on average.

In an exemplary embodiment, the non-amphiphilic nanocapsule may be one or more selected from a group consisting of a liposome, a polymersome, a nanoemulsion particle and a solid lipid nanoparticle (SLN).

In an exemplary embodiment, the non-amphiphilic nanocapsule may comprise one or more selected from a group consisting of a phospholipid, a wax, a butter and a ceramide.

In an exemplary embodiment, the non-amphiphilic nanocapsules may be included in the aqueous phase of the emulsion composition by being dispersed in an aqueous dispersion.

In an exemplary embodiment, the emulsion composition may include the oil phase and the aqueous dispersion including the non-amphiphilic nanocapsules at a weight ratio of 1:0.4-3.

In an exemplary embodiment, the aqueous dispersion including the non-amphiphilic nanocapsules may include water, a polyhydric alcohol and a lipid.

In an exemplary embodiment, the lipid may be one or more selected from a group consisting of a phospholipid, a wax, a butter and a ceramide.

In another aspect, the present disclosure provides a method for preparing the emulsion composition described above, which includes: a step of mixing an aqueous phase including water-dispersible non-amphiphilic nanocapsules and an oil phase; and a step of forming emulsion particles surrounded by the non-amphiphilic nanocapsules.

Advantageous Effects

In an aspect, the technology disclosed in the present disclosure has an effect of providing an emulsion composition which forms emulsion particles with water-dispersible non-amphiphilic nanocapsules without using a surfactant. Whereas water-dispersible nanocapsules have been previously used for the purpose of transdermal delivery or stabilization of active ingredients, the emulsion composition according to the present disclosure provides an effect of forming emulsion particles by using the water-dispersible nanocapsules for emulsification of the emulsion composition without additional modification of the physical properties. The emulsion composition according to the present disclosure can form emulsion particles in an oil-in-water emulsion composition without using a surfactant.

In another aspect, the technology disclosed in the present disclosure has an effect of providing the method for preparing an emulsion composition.

BRIEF DESCRIPTION OF DRAWINGS

FIGS. 9A-9D show a result of investigating the change of skin under a dry environment after application of a composition according to an exemplary embodiment of the present disclosure to the skin.

BEST MODE

Hereinafter, the technology disclosed in the present disclosure is described in detail.

In an aspect, the technology disclosed in the present disclosure provides an emulsion composition including emulsion particles formed by non-amphiphilic nanocapsules.

In another aspect, the technology disclosed in the present disclosure provides an emulsifying agent composition for forming emulsion particles, which includes non-amphiphilic nanocapsules as an active ingredient.

In another aspect, the technology disclosed in the present disclosure provides non-amphiphilic nanocapsules for use in preparation of an emulsion composition.

In another aspect, the technology disclosed in the present disclosure provides a use of non-amphiphilic nanocapsules in preparation of an emulsion composition.

In another aspect, the technology disclosed in the present disclosure provides non-amphiphilic nanocapsules for forming emulsion particles.

In another aspect, the technology disclosed in the present disclosure provides a use of non-amphiphilic nanocapsules for forming emulsion particles.

In another aspect, the technology disclosed in the present disclosure provides an emulsification method including a step of forming emulsion particles with non-amphiphilic nanocapsules.

In an exemplary embodiment, the emulsion composition may include emulsion particles.

In an exemplary embodiment, the emulsion particles may be surrounded by plurality of non-amphiphilic nanocapsules.

In an exemplary embodiment, the emulsion composition may include: an aqueous phase; and an oil phase, wherein a plurality of non-amphiphilic nanocapsules of two or more are located at the interface between the aqueous phase and the oil phase, and emulsion particles surrounded by the plurality of non-amphiphilic nanocapsules are formed.

In an exemplary embodiment, the emulsification method may include: a step of disposing a plurality of non-amphiphilic nanocapsules at the interface between an aqueous phase and an oil phase; and a step of forming emulsion particles surrounded by the non-amphiphilic nanocapsules.

In an exemplary embodiment, the emulsifying agent composition may be a water-dispersible aqueous dispersion including non-amphiphilic nanocapsules.

In an exemplary embodiment, the emulsion composition may not be one emulsified with a surfactant.

In an exemplary embodiment, the plurality of non-amphiphilic nanocapsules may be attached to each other at the interface between the aqueous phase and the oil phase to form emulsion particles.

In the present disclosure, the non-amphiphilic nanocapsules refer to nanocapsules that are not amphiphilic, and it means that the physical properties of the nanocapsules are not amphiphilic, which has a hydrophilic part and a hydrophobic part at the same time. For example, although the nanocapsules according to the present disclosure may be formed by amphiphilic materials such as phospholipids, the physical properties of the formed nanocapsules themselves do not exhibit amphiphilic property. Accordingly, it is not necessary to modify physical properties to provide Janus structure and, unlike the emulsion composition using the powder having the Janus structure, it can be used without being limited by the physical properties of the oil phase. In addition, the nanocapsules according to the present disclosure may have improved safety for skin because polyethylene glycol (PEG) is not used.

In the present disclosure, the nanocapsules refer to particles having a nanometer-scale size. The nanocapsule may be one with no distinction between an inner layer and an outer layer, or may have two or more layers. When the nanocapsule has two or more layers, an active ingredient for skin whitening, antioxidation, etc. may be included in the inner layer.

In an exemplary embodiment, the non-amphiphilic nanocapsules may have amorphous, spherical or oval shapes.

In an exemplary embodiment, the emulsion composition may be an oil-in-water type.

The emulsion composition according to the present disclosure does not exhibit an oil separation phenomenon when lyophilized and exhibits very superior formulation stability.

In an exemplary embodiment, the emulsion composition may not exhibit oil separation when it is prepared into a dried product by freezing at a temperature of −60° C. or lower, or −120 to −60° C., and then sublimating and eliminating water under reduced pressure, when checking with the naked eye.

In an exemplary embodiment, the freeze drying may be performed at a temperature of −120 to −100° C. or −120 to −110° C.

In an exemplary embodiment, the freeze drying may be performed at a pressure of 1-100 mTorr, 1-50 m Torr, 10-80 mTorr or 20-40 mTorr.

In an exemplary embodiment, the non-amphiphilic nanocapsules may have a particle size of 10 nm to 1 µm on average.

In an exemplary embodiment, the non-amphiphilic nanocapsules may have a particle size of 500 nm or smaller on average.

In an exemplary embodiment, the non-amphiphilic nanocapsules may have a particle size of 10-500 nm on average.

In an exemplary embodiment, the emulsion particles may have a particle size of 1-30 µm on average. In another exemplary embodiment, the emulsion particles may have a particle size of 1 µm or larger, 2 µm or larger, 3 µm or larger, 4 µm or larger, 5 µm or larger, 6 µm or larger, 7 µm or larger, 8 µm or larger, 9 µm or larger, 10 µm or larger, 11 µm or larger, 12 µm or larger, 13 µm or larger, 14 µm or larger or 15 µm or larger, and 30 µm or smaller, 29 µm or smaller, 28 µm or smaller, 27 µm or smaller, 26 µm or smaller, 25 µm or smaller, 24 µm or smaller, 23 µm or smaller, 22 µm or smaller, 21 µm or smaller, 20 µm or smaller, 19 µm or smaller, 18 µm or smaller, 17 µm or smaller, 16 µm or smaller, 15 µm or smaller, 14 µm or smaller, 13 µm or smaller, 12 µm or smaller, 11 µm or smaller or 10 µm or smaller, on average. For example, the emulsion particles may have a particle size of 2-30 µm, 5-30 µm, 2-20 µm, 5-20 µm, 2-10 µm, 5-10 µm or 2-15 µm, on average.

The emulsion particles prepared using the existing surfactant have a size of about 1-2 µm and aggregations occur between the emulsion particles. In contrast, the emulsion particles according to the present disclosure may have a size of 2 µm or larger and the aggregations do not occur between the emulsion particles.

In an exemplary embodiment, the particle size of the non-amphiphilic nanocapsules or the particle size of the emulsion particles may mean the diameter of the particles.

In an exemplary embodiment, the diameter may mean the longest diameter.

In an exemplary embodiment, the non-amphiphilic nanocapsule may be one or more selected from a group consisting of a liposome, a polymersome, a nanoemulsion particle and a solid lipid nanoparticle (SLN). The liposome, polymersome, nanoemulsion particle and solid lipid nanoparticle may be prepared according to common preparation methods well known in the art.

In an exemplary embodiment, the non-amphiphilic nanocapsules may be nanoemulsion particles. The nanoemulsion particles can encapsulate an active ingredient and may have a very superior effect of delivering the active ingredient to the skin.

In an exemplary embodiment, the non-amphiphilic nanocapsule may comprise one or more selected from a group consisting of a phospholipid, a wax, a butter and a ceramide, and may be used to form emulsion particles without modification of the physical properties of the nanocapsule.

In an exemplary embodiment, the phospholipid may be one or more selected from a group consisting of hydrogenated lecithin, hydrogenated phosphatidylcholine, soybean phospholipid, hydrogenated lysophosphatidylcholine, hydrogenated lysolecithin and unsaturated lecithin.

In an exemplary embodiment, the wax may be one or more selected from a group consisting of a plant wax, an animal wax, a mineral wax and a synthetic wax.

In an exemplary embodiment, the wax may be one or more selected from a group consisting of candelilla wax, carnauba wax, ozokerite, ceresin wax, montan wax, microcrystalline wax, tribehenin, glyceryl behenate, glyceryl dibehenate, glyceryl tribehenate, stearyl behenate and trihydroxystearin.

In an exemplary embodiment, the butter may be one or more selected from a group consisting of shea butter, cocoa butter, almond butter, apricot butter, peach butter, cupuacu butter, pistachio butter, olive butter, aloe butter, vanilla butter, illipe butter, camellia butter, babassu butter, avocado butter, jojoba butter, kokum butter, cacao butter, mango butter, bean butter, grape seed butter, kokum butter, murumuru butter and macadamia seed butter.

In an exemplary embodiment, the ceramide may be a natural ceramide, a synthetic ceramide or a pseudo-ceramide.

The pseudo-ceramide is a synthetic substance which is structurally similar to the natural ceramide and exhibits similar properties with the natural ceramide such as protection of skin, maintenance of moisture, etc. For example, it may be hydroxypropyl bispalmitamide MEA, although not being limited thereto.

In an exemplary embodiment, the non-amphiphilic nanocapsules may be included in the aqueous phase of the emulsion composition by being dispersed in an aqueous dispersion.

In an exemplary embodiment, an aqueous dispersion including non-amphiphilic nanocapsules may be included in the aqueous phase, and the non-amphiphilic nanocapsule may be positioned at the interface between the aqueous phase and the oil phase of the emulsion composition to form emulsion particles.

In an exemplary embodiment, the non-amphiphilic nanocapsules may be water-dispersible non-amphiphilic nanocapsules. Accordingly, the emulsion composition according to the present disclosure may include: an aqueous phase including water-dispersible non-amphiphilic nanocapsules; and an oil phase, and the plurality of non-amphiphilic nanocapsules may form emulsion particles.

In the present disclosure, the water-dispersible non-amphiphilic nanocapsules may refer to non-amphiphilic nanocapsules existing in a dispersed state in an aqueous phase, and the water-dispersible non-amphiphilic nanocapsules may refer to an aqueous dispersion including non-amphiphilic nanocapsules.

In an exemplary embodiment, the emulsion composition may include the oil phase and the aqueous dispersion including the non-amphiphilic nanocapsules at a weight ratio of 1:0.4-3. Through this, there is an effect of preventing a problem that the content of the water-dispersible non-amphiphilic nanocapsules is too small, so the formulation stability may be degraded. In addition, there is an effect of preventing a problem that the content of the water-dispersible non-amphiphilic nanocapsules is too large, so the feeling of use may be degraded due to poor spreadability, applicability and absorption.

In an exemplary embodiment, the water-dispersible non-amphiphilic nanocapsules (i.e., the aqueous dispersion including non-amphiphilic nanocapsules) added to and mixed with the aqueous phase of the emulsion composition may include water, a polyhydric alcohol and a lipid.

In an exemplary embodiment, the water-dispersible non-amphiphilic nanocapsules (i.e., the aqueous dispersion including non-amphiphilic nanocapsules) added to and mixed with the aqueous phase of the emulsion composition may include: 45-90 wt % of an aqueous phase part; and 1-55 wt % of an oil phase part including a lipid, based on the total weight of the aqueous dispersion.

In an exemplary embodiment, the lipid may be included in an amount of 1-30 wt % based on the total weight of the aqueous dispersion. In another exemplary embodiment, the lipid may be included in an amount of 1 wt % or more, 3 wt % or more, 5 wt % or more, 7 wt % or more, 9 wt % or more, 11 wt % or more, 13 wt % or more or 15 wt % or more, and 30 wt % or less, 28 wt % or less, 26 wt % or less, 24 wt % or less, 22 wt % or less or 20 wt % or less, based on the total weight of the aqueous dispersion.

In an exemplary embodiment, the aqueous phase part may include a polyhydric alcohol.

In an exemplary embodiment, the oil phase part may include one or more selected from a group consisting of a polyhydric alcohol, an emulsifier and an oil.

In an exemplary embodiment, the water-dispersible non-amphiphilic nanocapsules (i.e., the aqueous dispersion including non-amphiphilic nanocapsules) added to and mixed with the aqueous phase of the emulsion composition may include: 45-75 wt % of an aqueous phase part; and 25-55 wt % of an oil phase part including a polyhydric alcohol, a lipid and an emulsifier.

Specifically, in an exemplary embodiment, the polyhydric alcohol, the lipid and the emulsifier may be mixed in amounts of 40-55 wt %, 30-50 wt % and 10-20 wt %, respectively, based on the total weight of the oil phase part, for easier formation of emulsion particles.

In an exemplary embodiment, the lipid may include a phospholipid and a wax, and the phospholipid and the wax may be mixed at a weight ratio of 1:9-18 for easier formation of emulsion particles and better formulation stability.

In an exemplary embodiment, the lipid may further include a ceramide, and the ceramide may be mixed with the phospholipid at a weight ratio of 1:3 to 3:1.

In an exemplary embodiment, the water-dispersible non-amphiphilic nanocapsules (i.e., the aqueous dispersion including non-amphiphilic nanocapsules) added to and mixed with the aqueous phase of the emulsion composition may include: 70-90 wt % of an aqueous phase part including a polyhydric alcohol; and 10-30 wt % of an oil phase part including an oil and a lipid.

In an exemplary embodiment, the lipid may be one or more selected from a group consisting of a phospholipid, a wax, a butter and a ceramide.

In an exemplary embodiment, the polyhydric alcohol may be one or more selected from a group consisting of butylene glycol, propylene glycol, glycerin, pentylene glycol, dipropylene glycol and diglycerin.

In an exemplary embodiment, the emulsifier may be one or more selected from a group consisting of sorbitan sesquioleate, glyceryl stearate, polysorbate 60, polysorbate 80, sorbitan stearate, PEG-20 glyceryl isostearate, polyglyceryl-2 diisostearate, cetearyl alcohol, polyglyceryl-3-methylglucose distearate, PEG-100 stearate, sorbitan isostearate, lauryl glucoside, disodium cocoamphodiacetate, coconut fatty acid diethanolamide and cocamidopropyl betaine.

In an exemplary embodiment, the oil may be one or more selected from a group consisting of a vegetable oil, a silicone-based oil, an ester-based oil and a hydrocarbon-based oil.

In an exemplary embodiment, the vegetable oil may be one or more selected from a group consisting of olive oil, camellia oil, castor oil, jojoba oil, almond oil, grape seed oil, herb oil, rose oil, coconut oil, avocado oil, macadamia oil, moringa oil, rice bran oil, apricot seed oil, sunflower oil, meadowfoam seed oil and abyssinian oil.

In an exemplary embodiment, the silicone-based oil may be one or more selected from a group consisting of dimethylpolysiloxane, methylphenylpolysiloxane, decamethylcyclopentasiloxane, methyl trimethicone, phenyl trimethicone, cyclomethicone and dimethicone.

In an exemplary embodiment, the ester-based oil may be one or more selected from a group consisting of isopropyl palmitate, 2-octyldodecyl myristate, isopropyl myristate, butyloctyl salicylate, cetyl octanoate, cetyl octylhexanoate, coco-caprylate/caprate, decyl cocoate, isostearyl isostearate, pentaerythrityl tetraethylhexanoate and dicaprylyl carbonate.

In an exemplary embodiment, the hydrocarbon-based oil may be one or more selected from a group consisting of n-octane, n-nonane, n-decane, n-undecane, n-dodecane, n-tridecane, n-tetradecane, n-pentadecane, n-hexadecane, n-heptadecane, n-octadecane, vaseline, paraffin, ceresin, hydrogenated polydecene, hydrogenated polyisobutene and squalane.

In another aspect, the technology disclosed in the present disclosure provides a method for preparing the water-dispersible non-amphiphilic nanocapsules, which includes: a step of mixing and dissolving an aqueous phase part; a step of mixing and dissolving an oil phase part; and a step of adding the oil phase part to the aqueous phase part, dispersing with a homogenizer and then cooling.

The homogenizer may be any one without limitation as long as it can provide sufficient energy for dispersing a dissolved oleophilic mixture phase to prepare nanocapsules with a particle size of 10 nm to 1 μm. In particular, in order to form the nanocapsule particles of lipids, an ultrasonic and high-pressure homogenizer may be preferred.

The emulsion composition does no use an additional surfactant for emulsification of the emulsion composition except for the surfactant used to prepare the nanocapsules. Therefore, because switching with the surfactant present in the outer phase of the emulsion composition does not occur, the stability of the nanocapsules and the emulsion particles can be maintained longer in the formulation. Accordingly, the emulsion composition exhibits very superior formulation stability with regard to freezing and thawing. In addition, since the water-dispersible non-amphiphilic nanocapsules can be easily produced in large scales, the disadvantage of the existing emulsification method of stabilizing powder at the interface can be improved.

The emulsion composition can improve skin roughness and maintain high skin water content by inhibiting water evaporation by occlusive effect at the same time because, when applied to skin, the nanocapsules present at the interface are packed on the skin surface. In addition, when an active ingredient is encapsulated in the non-amphiphilic nanocapsules, the delivery of the active ingredient to the skin may be improved. The nanocapsules according to the present disclosure may be designed variously depending on sensation of use, effect, purpose, etc.

In another aspect, the technology disclosed in the present disclosure provides a method for preparing the emulsion composition, which includes: a step of mixing an aqueous phase including water-dispersible non-amphiphilic nanocapsules with an oil phase; and a step of forming emulsion particles surrounded by the non-amphiphilic nanocapsules by attaching the non-amphiphilic nanocapsules with each other.

MODE FOR INVENTION

Hereinafter, the present disclosure will be described in more detail through examples. The following examples are for illustration of the present disclosure only, and it will be obvious to those having ordinary knowledge in the art that the scope of the present disclosure should not be interpreted as being limited by the examples.

Examples 1-1 and 1-2. Preparation of Water-Dispersible Non-Amphiphilic Nanocapsules Water-dispersible non-amphiphilic nanocapsules were prepared according to the compositions (wt %) described in Tables 1 and 2 and used. Specifically, an oleophilic mixture was prepared by heating and dissolving an oil phase part at 70° C. and then dispersing with a homogenizer. After heating and dissolving an aqueous phase part in a separate container at 70° C., capsule particles were formed at 70° C. using a homogenizer by slowly adding the prepared oleophilic mixture to the aqueous phase part. Then, nanocapsule particles were formed by cooling due to recrystallization of lipids. Water-dispersible non-amphiphilic nanocapsules in the form of solid lipid nanoparticles (Example 1-1) and nanoemulsion particles (Example 1-2) were prepared to a particle size of 10 nm to 1 μm using an ultrasonic, high-pressure homogenizer.

TABLE 1

|  |  | Example 1-1 |
|---|---|---|
| Aqueous phase | Water | To 100 |
|  | 1,2-Hexanediol | 1 |
|  | Ethylhexylglycerin | 0.05 |
| Oil phase | Butylene glycol | 20 |
|  | Hydroxypropyl bispalmitamide MEA | 1 |
|  | Polyglyceryl-3-methylglucose distearate | 7 |
|  | Hydrogenated lecithin | 1 |
|  | Stearyl behenate | 13 |

TABLE 2

|  |  | Example 1-2 |
|---|---|---|
| Aqueous phase | Water | To 100 |
|  | Ethylhexylglycerin | 0.05 |
|  | 1,2-Hexanediol | 1.5 |
|  | Butylene glycol | 10 |
| Oil phase | Meadowfoam seed oil | 6.0 |
|  | Ceramide 3 | 1.0 |
|  | Cholesterol | 1.0 |
|  | Stearic acid + palmitic acid | 0.8 |
|  | Hydrogenated lecithin | 3 |
|  | Shea butter | 5.5 |
|  | Tocopherol | 0.5 |

Examples 2-10 and Comparative Example 1. Preparation of Emulsion Composition Emulsion compositions were prepared as follows according to the composition (wt %) described in Table 3.
1) The aqueous phase part including water, water-dispersible non-amphiphilic nanocapsules, 1,2-hexanediol, ethylhexyl glycerin, carbomer and tromethamine was mixed and dissolved by heating to 50-75° C.
2) The remaining oil phase part was mixed and dissolved by heating to 50-7° C.
3) An emulsion composition was prepared using a homogenizer after adding the oil phase part to the aqueous phase part while maintaining the temperature at 50-75° C.

TABLE 3

| INCI | Ex. 2 | Ex. 3 | Ex. 4 | Ex. 5 | Ex. 6 | Ex. 7 | Ex. 8 | Ex. 9 | Ex. 10 | Ex. 11 | Comp. Ex. 1 |
|---|---|---|---|---|---|---|---|---|---|---|---|
| Squalane |  | 10 | 10 |  |  |  |  |  |  |  |  |
| Sunflower (Helianthus annuus) seed oil | 3 | 3 | 3 | 3 | 3 | 3 | 3 | 3 | 3 | 3 | 3 |
| Hydrogenated C$_{6-14}$ olefin polymers | 10 | 5 |  |  |  | 2 | 10 | 10 | 10 | 10 | 10 |
| Pentaerythrityl tetraethylhexanoate |  | 10 |  | 10 |  |  |  |  |  |  |  |
| Dicaprylyl carbonate + tocopherol + wild soybean (Glycine soja) oil |  |  |  |  | 10 |  |  |  |  |  |  |
| Cyclopentasiloxane + cyclohexasiloxane | 2 | 2 | 2 | 2 | 2 | 2 | 2 | 2 | 2 | 2 | 2 |
| Water |  |  |  |  |  | To 100 |  |  |  |  |  |
| Water-dispersible non-amphiphilic nanocapsules of Example 1-1 | 10 | 50 | 10 | 10 | 10 | 5 | 20 | 30 | 40 |  | 5 |
| Water-dispersible non-amphiphilic nanocapsules of Example 1-2 |  |  |  |  |  |  |  |  |  | 10 |  |

TABLE 3-continued

| INCI | Ex. 2 | Ex. 3 | Ex. 4 | Ex. 5 | Ex. 6 | Ex. 7 | Ex. 8 | Ex. 9 | Ex. 10 | Ex. 11 | Comp. Ex. 1 |
|---|---|---|---|---|---|---|---|---|---|---|---|
| 1,2-Hexanediol | 1 | 1 | 1 | 1 | 1 | 1 | 1 | 1 | 1 | 1 | 1 |
| Ethylhexylglycerin | 0.05 | 0.05 | 0.05 | 0.05 | 0.05 | 0.05 | 0.05 | 0.05 | 0.05 | 0.05 | 0.05 |
| Carbomer | 0.2 | 0.2 | 0.2 | 0.2 | 0.2 | 0.2 | 0.2 | 0.2 | 0.2 | 0.2 | 0.2 |
| Tromethamine | 0.1 | 0.1 | 0.1 | 0.1 | 0.1 | 0.1 | 0.1 | 0.1 | 0.1 | 0.1 | 0.1 |

Test Example 1

A result of evaluating the spreadability when applied, applicability when applied, moisture maintenance, transdermal absorption and formulation stability of the prepared emulsion compositions is shown in Table 4.

TABLE 4

| | Ex. 2 | Ex. 3 | Ex. 4 | Ex. 5 | Ex. 6 | Ex. 7 | Ex. 8 | Ex. 9 | Ex. 10 | Comp. Ex. 1 |
|---|---|---|---|---|---|---|---|---|---|---|
| Spreadability when applied | ◎ | ○ | ◎ | ◎ | ◉ | ◎ | ◎ | ◉ | ○ | ◉ |
| Applicability when applied | ◎ | ○ | ◎ | ◎ | ◉ | ◎ | ◎ | ◉ | ○ | ◉ |
| Moisture maintenance | ◎ | ◉ | ◎ | ◎ | △ | △ | ◎ | ◉ | ◎ | ○ |
| Transdermal absorption | ◎ | ◉ | ◎ | ◎ | ○ | △ | ◎ | ◉ | ◎ | △ |
| Formulation stability | ◎ | ◉ | ◎ | ◎ | ◉ | ◎ | ◎ | ◉ | ◎ | △ |

◉: superior, ○: good, △: insufficient

To compare Examples 2 and 4-6, it was confirmed that emulsification is possible using the non-amphiphilic nanocapsules regardless of the type or polarity of oils and the emulsion compositions show good formulation stability. Accordingly, it was confirmed that the water-dispersible non-amphiphilic nanocapsules according to the present disclosure can be used to form emulsion particles without being limited by the oil phase.

In addition, as a result of investigating formulation stability depending on the content of the water-dispersible non-amphiphilic nanocapsules and the content of the oil for Examples 2, 3 and 7 and Comparative Example 1, it was confirmed that it is preferred in terms of formulation stability to increase the content of the water-dispersible non-amphiphilic nanocapsules to be positioned at the water-oil interface as the content of the oil is increased. The unsatisfactory moisture maintenance and absorption for Example 7 seem to be due to the relatively low contents of the oil and the non-amphiphilic nanocapsules.

In addition, from comparison of Examples 2 and 8-10, it was confirmed that the sensation of use can be controlled with the content of the non-amphiphilic nanocapsules since the content of the water-dispersible non-amphiphilic nanocapsules affects spreadability and applicability during initial application.

Test Example 2

In order to investigate the emulsion particle structure of the emulsion composition, water-dispersible non-amphiphilic nanocapsules were prepared in the same manner as in Example 1-1 by adding a fluorescent dye (Nile red, 515-560 nm excitation; >590 nm emission) during the preparation of the nanocapsules and an emulsion composition prepared in the same manner as in Example 2 was observed under a microscope.

Figure 1A:
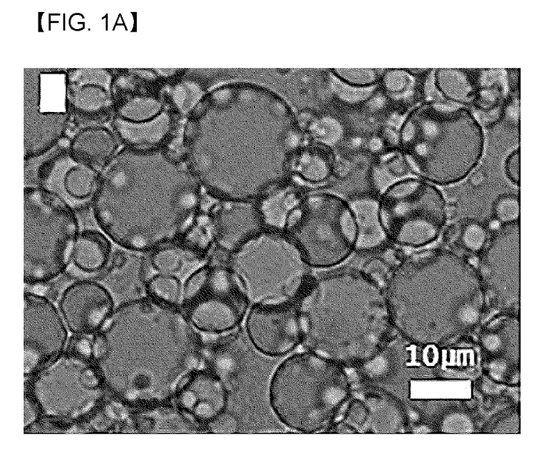
FIG. 1A shows the polarized light microscopic image of an emulsion composition according to an exemplary embodiment of the present disclosure.
Figure 1B:
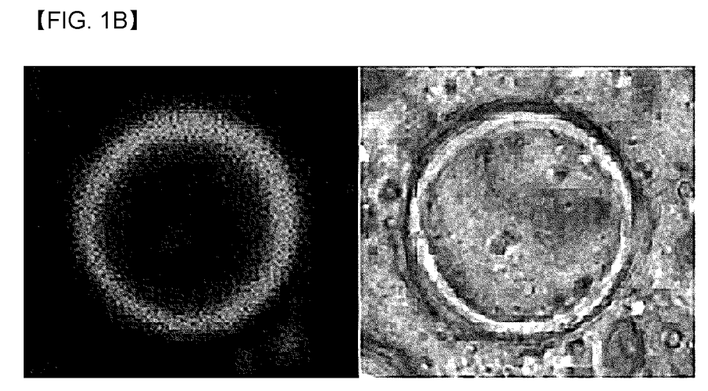
FIG. 1B shows the confocal microscopic images of an emulsion composition according to an exemplary embodiment of the present disclosure.

FIG. 1A shows an image obtained with a polarized light microscope (LV100POL) and FIG. 1B shows an image obtained with a laser confocal microscope (VIVASCOPE 1500). It was observed that the fluorescent dye-labeled nanocapsules are located at the interface of the emulsion particles. It was confirmed that the emulsion composition according to the present disclosure can form emulsion particles by stabilizing the nanocapsule at the interface between the aqueous phase and the oil phase without using a surfactant.

Test Example 3

Figure 2:
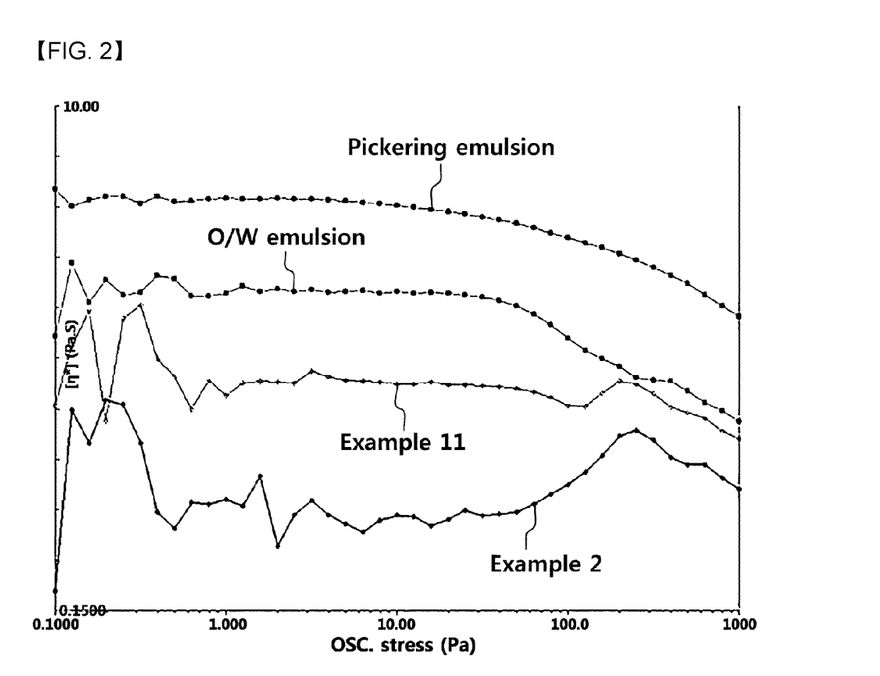
FIG. 2 compares the rheology measurements result of an emulsion composition according to an exemplary embodiment of the present disclosure with the existing O/W emulsion and Pickering emulsion. The results for a Pickering emulsion, an O/W emulsion, a composition of Example 11 and a composition of Example 2 are shown from top to bottom.

The rheology of the emulsion compositions of Examples 2 and 11 using the nanocapsules according to the present disclosure and an O/W emulsion and a Pickering emulsion as the existing emulsion compositions was measured and compared (measurement apparatus: rheometer (AR2000), measurement condition: OSC stress (Pa) 0.1-1000 @ frequency 50 Hz). As a result, it was found out that the emulsion compositions of Examples 2 and 11 according to the present disclosure have yield stress values (see FIG. 2). This means that unlike other formulations, initial bursting sensation of use, that is sensation of use of initial water burst can be felt. In addition, viscosity was increased at a later stage as in the shear thickening phenomenon. It is because the characteristics of the nanocapsules appear at the later stage. The emulsion compositions according to the present disclosure showed a smooth finish feeling due to the application of the nanocapsule particles and exhibited an effect of improving skin roughness and moisturizing the skin.

As described above, it was confirmed that the compositions of Examples 2 and 11 have distinct characteristics in structure and sensation of use as compared to the existing emulsion formulations. The O/W emulsion and Pickering emulsion used in the experiment were prepared as follows.

Preparation of O/W Emulsion

The O/W emulsion was prepared according to a common method with the composition (wt %) described in Table 5.

TABLE 5

| INCI | Contents |
| --- | --- |
| PEG-100 stearate + glyceryl stearate | 5.00 |
| Squalane | 7.00 |
| Diisostearyl malate | 5.00 |
| Dimethicone | 4.00 |
| Purified water | To 100 |
| Disodium EDTA | 0.05 |
| Glycerin | 0.50 |
| Glyceryl caprylate | 0.10 |
| Ethylhexylglycerin | 0.05 |
| Behenyl alcohol | 2.00 |
| Fragrance | 0.05 |
| Purified water + sorbitan isostearate + polyacrylate 13 + polyisobutene + polysorbate 20 | 0.43 |

Preparation of Pickering Emulsion

The Pickering emulsion was prepared according to a common method with the composition (wt %) described in Table 6.

TABLE 6

| INCI | Contents |
| --- | --- |
| Purified water | To 100 |
| Disodium EDTA | 0.05 |
| butylene glycol | 10.00 |
| Phenoxyethanol | 0.20 |
| Ethylhexylglycerin | 0.05 |
| $C_{12-15}$ alkyl benzoate | 5.00 |
| Ethylhexyl methoxycinnamate | 3.00 |
| Bis-ethylhexyloxyphenol methoxyphenyl triazine | 3.00 |
| Cyclopentasiloxane + cyclohexasiloxane | 5.00 |
| Silica | 2.00 |
| Titanium dioxide + stearic acid + alumina | 2.00 |
| Fragrance | 0.25 |
| Purified water + sorbitan isostearate + polyacrylate 13 + polyisobutene + polysorbate 20 | 1.00 |

Test Example 4

After applying the emulsion composition prepared in Example 2 to skin, the change in skin texture and moisture was observed.

Figure 3:
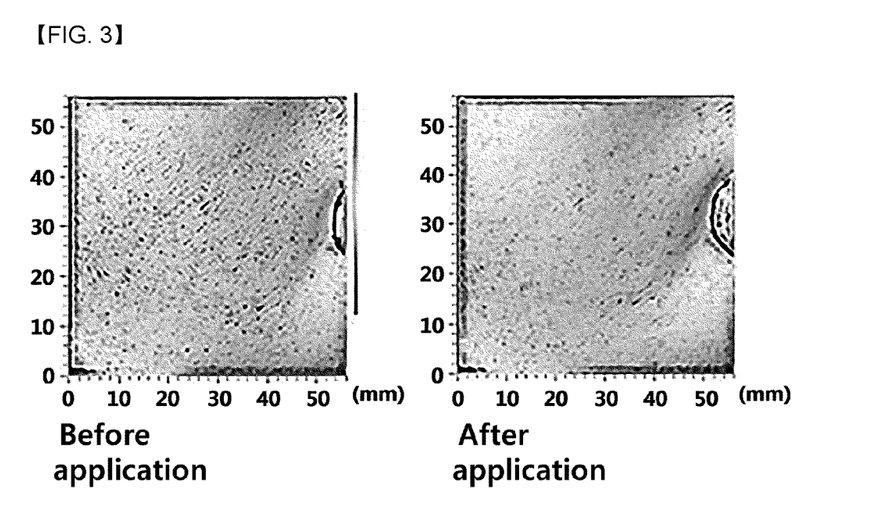
FIG. 3 shows a result of investigating the change in skin texture before and after application of an emulsion composition according to an exemplary embodiment of the present disclosure to skin.
Figure 4:
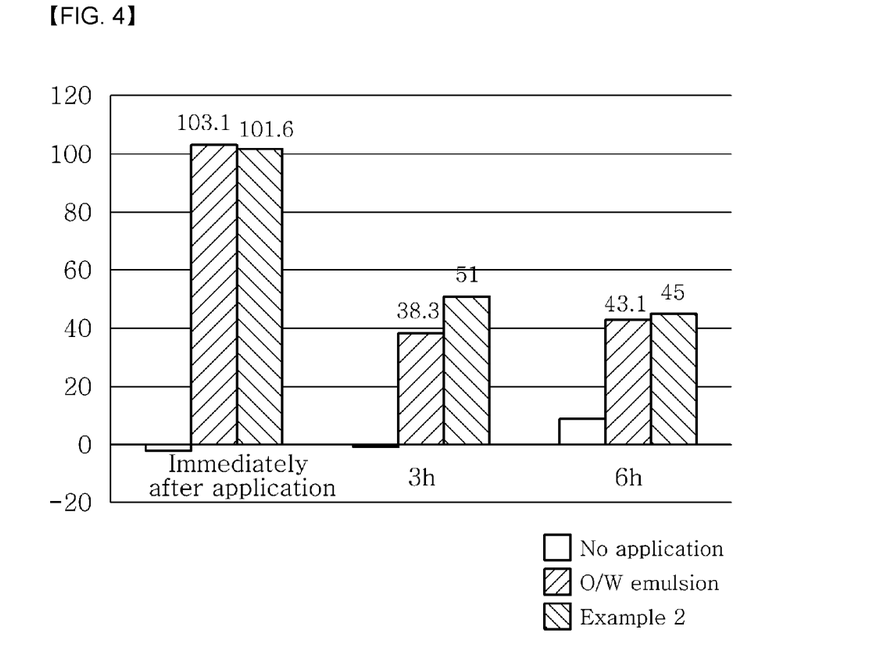
FIG. 4 shows a result of investigating the change in skin water content (%) depending on the application of an emulsion composition according to an exemplary embodiment of the present disclosure to skin.

As seen from FIG. 3, it was confirmed that skin roughness was decreased by 14.4% when the emulsion composition of Example 2 was applied to the skin as compared to before the application. In addition, as seen from FIG. 4, it was confirmed that moisture is maintained longer in the skin when the emulsion composition of Example 2 was applied to the skin as compared to when no composition was applied or when the O/W emulsion of Test Example 3 was applied. It is because the nanocapsules forming emulsion particles burst and are packed on the skin when applied to the skin, thereby preventing water loss and providing smooth skin texture.

Test Example 5

After freeze-drying the emulsion composition prepared in Example 2 and the O/W emulsion of Test Example 3, their formulation stability was compared.

Figure 5:
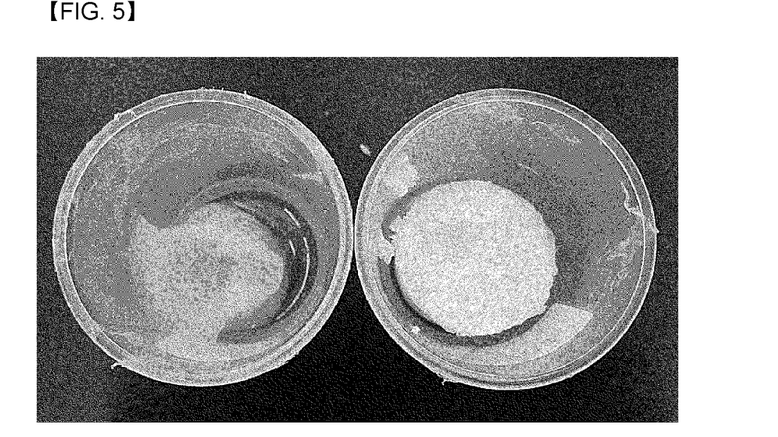
FIG. 5 shows a result of investigating the formulation stability of an emulsion composition according to an exemplary embodiment of the present disclosure and the existing O/W emulsion after freeze drying.

Freeze drying is a drying process of preparing a dried product by freezing a material and sublimating ice directly into vapor by lowering the partial pressure of water vapor. After freezing the emulsion composition of Example 2 and the O/W emulsion of Test Example 3 at a temperature of −80° C. or lower using a freezer and transferring to a drier, freeze-dried samples were obtained as in FIG. 5 (left: the O/W emulsion of Test Example 3, right: the emulsion composition of Example 2) by sublimation.

The freeze-drying process is advantageous in that it can be processed into powder form and rehydrated at the stage of use. It can be utilized for stabilization of active ingredients and in various forms of cosmetics. It was confirmed that general emulsions such as the O/W emulsion of Test Example 3 cannot be freeze-dried because oil oozes out during the freeze drying process together with shrinkage and deformation of appearance. In contrast, it was confirmed that the emulsion composition of Example 2 maintains the structure of emulsion particles without separation of oil during freeze drying and exhibits superior formulation stability. General emulsions require other efforts to maintain the structure of emulsion particles, which often result in unsatisfactory sensation of use. But, when the nanocapsules according to the present disclosure are used, superior formulation stability and superior sensation of use can be achieved without using other materials because the emulsion particles are packed by nanocapsules and maintain their structure well.

Test Example 6

Figure 6:
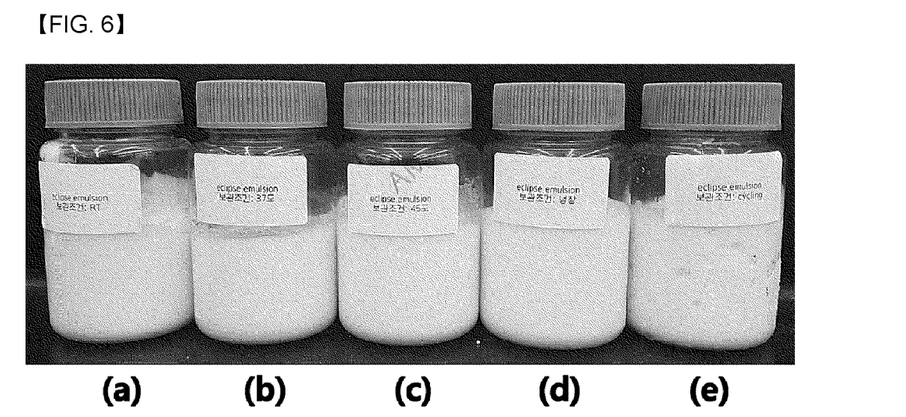
FIG. 6 shows a result of investigating the formulation stability of an emulsion composition according to an exemplary embodiment of the present disclosure depending on change in temperature. The results of storing the emulsion composition under the conditions of (a) room temperature, (b) 37° C., (c) 45° C., (d) refrigeration and (e) cycling, respectively, for 4 weeks are shown.

A result of observing the change of the formulation stability of the emulsion composition prepared in Example 2 depending on temperature is shown in FIG. 6. It was confirmed that formulation stability is maintained when it is stored under the condition of room temperature, 37° C., 45° C. and refrigeration for 4 weeks, respectively. In addition, it was confirmed that formulation stability is maintained without oil separation during cycling storage at a cycle of 12 hours for a total of 4 weeks by applying a temperature change from 40° C. to −10° C. or from −10° C. to 40° C. over 12 hours.

In addition, the formulation stability of the emulsion composition prepared in Example 2 was observed though viscosity measurement according to changes over time. The result is given in Table 7. The viscosity was measured using a viscometer (Brookfield Viscometer, LVDV-2+P) about samples stored at 30° C. (measurement condition: S64 spindle, 12 rpm, measurement for 2 minutes).

TABLE 7

| Change with the passage of time (viscosity) | |
| --- | --- |
| | Example 2 |
| Immediately after preparation | 12500 cps |
| 1 week later | 14800 cps |
| 2 weeks later | 15600 cps |
| 3 weeks later | 14500 cps |
| 4 weeks later | 15300 cps |

Test Example 7

Figure 7:
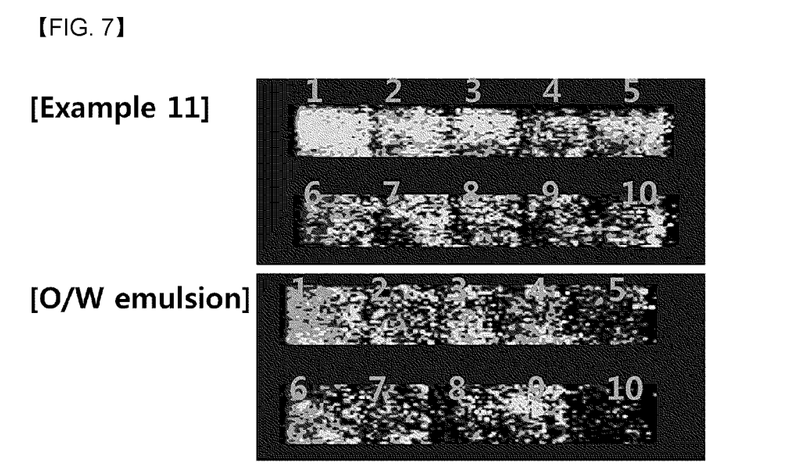
FIG. 7 shows a result of comparing the delivery effect of an active ingredient in a test example according to the present disclosure.

FIG. 7 shows a result of investigating the delivery effect of tocopherol encapsulated as an active ingredient in the nanocapsules of the emulsion composition prepared in Example 11. The delivery effect of the active ingredient was compared with an OW emulsion prepared by adding 0.5 wt % of tocopherol to the O/W emulsion of Test Example 3.

For investigation of the delivery effect of the active ingredient, each composition was applied onto skin. After waiting for 3 hours and wiping out the composition remaining on the skin, samples were prepared by taping 10 sheets with stripping tapes for skin keratin collection (D-Squame Stripping Discs D101, CUDERM). The dermal delivery effect was investigated by imaging the active ingredient tocopherol attached to the tapes by DESI-MS (instrument: QTOF-MS (Q-Time-of-Flight Mass Spectrometer)) imaging.

As a result, it was confirmed that the tocopherol included in the emulsion composition of Example 11 is delivered deeper into the skin as compared to the active ingredient included in the O/W emulsion of Test Example 3. In FIG. 7, the bright yellow regions indicate the active ingredient.

Test Example 8

Figure 8:
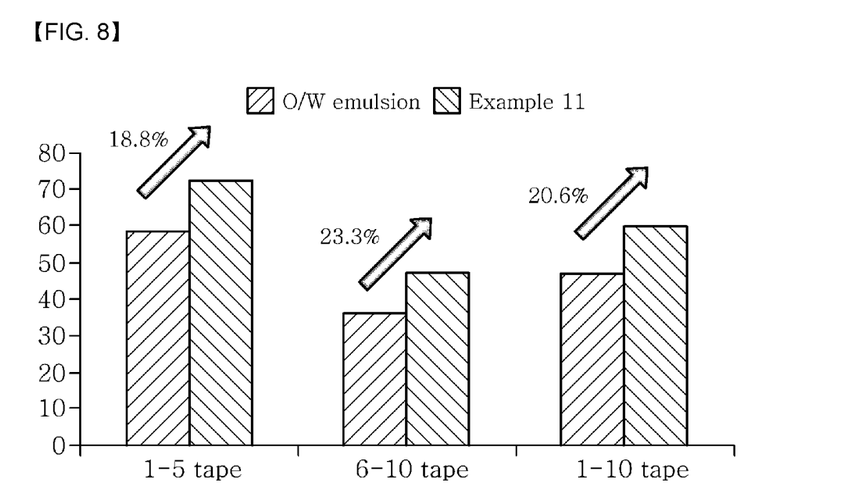
FIG. 8 shows a result of comparing the skin absorption of an active ingredient in a test example according to the present disclosure.
Figure 9A:
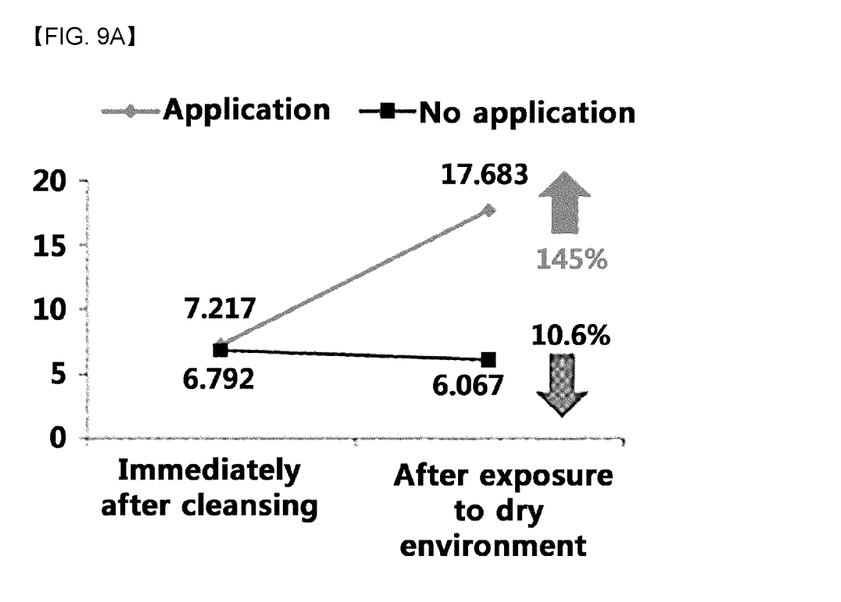
FIG. 9A shows the change in skin water content.
Figure 9B:
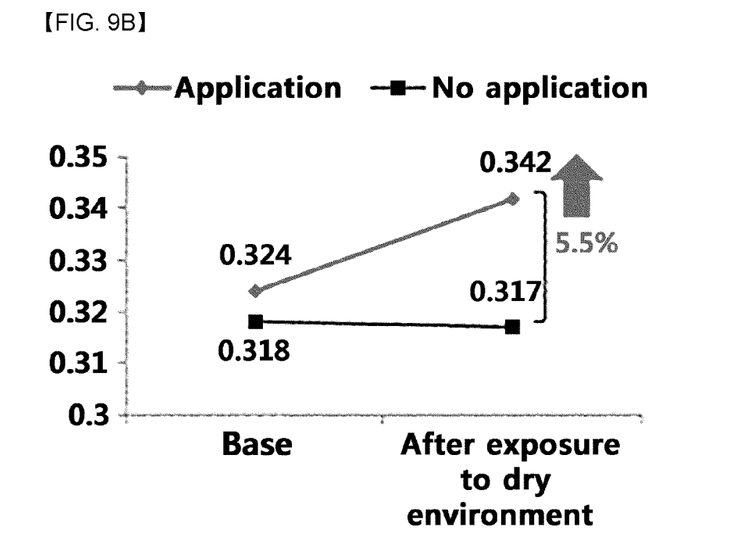
FIG. 9B shows the change in the flexibility of the skin around eyes.
Figure 9C:
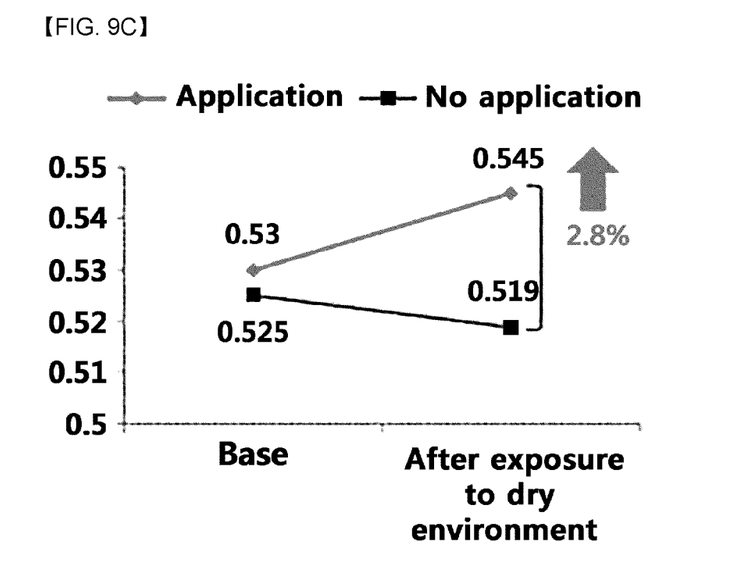
FIG. 9C shows the change in the elasticity of the skin around eyes (R5) and FIG. 9D shows the change in the wrinkles around eyes (Ra).
Figure 9D:
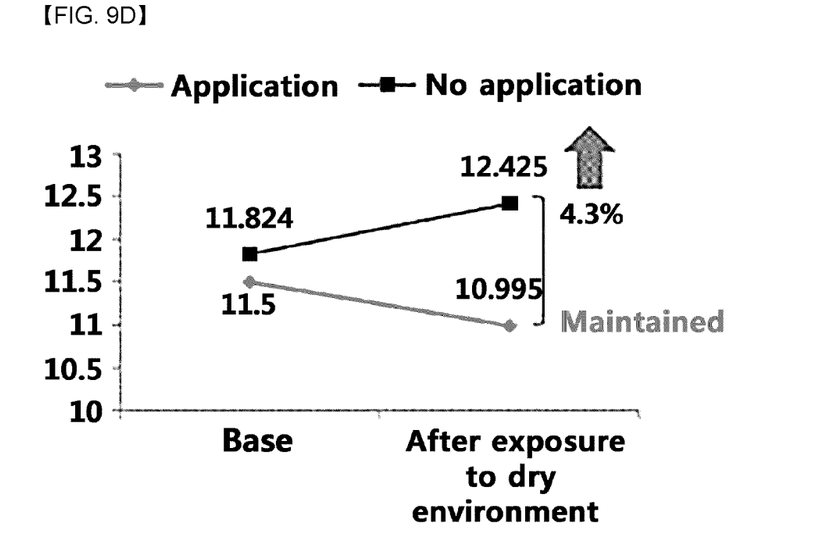

A result of investigating transdermal absorption of tocopherol included as an active ingredient in the nanocapsules of the emulsion composition prepared in Example 11 is shown in FIG. 8. The transdermal absorption of the active ingredient was compared with an O/W emulsion prepared by adding 0.5 wt % of tocopherol to the O/W emulsion of Test Example 3.

For investigation of the transdermal absorption of the active ingredient, each composition was applied onto skin. After waiting for 3 hours and wiping out the composition remaining on the skin, samples were prepared by taping 10 sheets with stripping tapes for skin keratin collection (D-Squame Stripping Discs D101, CUDERM). The transdermal absorption was determined by analyzing the amount of the active ingredient tocopherol attached to the tapes by HPLC (instrument: Waters e2695, column: SunFire Silica (4.6×250 mm×5 μm), hexane: isopropanol=99:1, flow rate: 0.7 mL/min, 325 nm).

As a result, it was confirmed that the transdermal absorption of tocopherol included in the emulsion composition of Example 11 is higher than the transdermal absorption of tocopherol included in the O/W emulsion of Test Example 3. In FIG. 8, 1-5 tape, 6-10 tape and 1-10 tape indicate average values for tapes 1-5, tapes 6-10 and tapes 1-10, respectively, and the y-axis represents the measured absorption amount (%).

Test Example 9

After applying the emulsion composition prepared in Example 11 onto skin, the change in the skin water content, the flexibility of the skin around eyes, the elasticity of the skin around eyes and the wrinkles around eyes was investigated under dry environment. The result is shown in FIGS. 9A-9D. The dry environment was made by waiting for 1 hour under a condition of less than 35% relative humidity. As a result, unlike the test group in which the composition was not applied, the application of the emulsion composition of Example 11 was effective in increasing the skin water content, the flexibility of the skin around eyes and the elasticity of the skin around eyes and preventing the wrinkles around eyes even under dry environment.

Although the specific exemplary embodiments of the present disclosure have been described in detail, it will be obvious to those having ordinary knowledge in the art that the specific exemplary embodiments are merely preferred examples and that the scope of the present disclosure is not limited by them. It is to be understood that the substantial scope of the present disclosure is defined by the appended claims and their equivalents.

The invention claimed is:

1. An emulsion composition comprising:
an aqueous phase; and
an oil phase,
wherein
a plurality of non-amphiphilic nanocapsules are located at the interface between the aqueous phase and the oil phase,
the plurality of non-amphiphilic nanocapsules are attached to each other,
emulsion particles surrounded by the plurality of non-amphiphilic nanocapsules are formed,
the emulsion composition is an oil-in-water type,
the emulsion composition is obtained by mixing the aqueous phase comprising an aqueous dispersion with the oil phase,
the aqueous dispersion comprises water-dispersible non-amphiphilic nanocapsules formed by mixing an aqueous phase part and an oil phase part, and
a weight ratio of the oil phase of the emulsion composition and the aqueous dispersion is 1:0.4-3.

2. The emulsion composition according to claim 1, wherein the emulsion composition does not exhibit oil separation when it is prepared into a dried product by freezing at a temperature of −60° C. or lower, and then sublimating and eliminating water under reduced pressure.

3. The emulsion composition according to claim 1, wherein the non-amphiphilic nanocapsules have a particle size of 10 nm to 1 μm on average.

4. The emulsion composition according to claim 1, wherein the emulsion particles have a particle size of 1-30 μm on average.

5. The emulsion composition according to claim 1, wherein the non-amphiphilic nanocapsule is one or more selected from the group consisting of a liposome, a polymersome, a nanoemulsion particle and a solid lipid nanoparticle (SLN).

6. The emulsion composition according to claim 1, wherein the aqueous phase part and the oil phase part are mixed in an amount of 45-75 wt % and 25-55 wt %, respectively, based on the total weight of the aqueous dispersion, and
the aqueous phase part comprises a polyhydric alcohol, and the oil phase part comprises a polyhydric alcohol, a lipid and an emulsifier.

7. The emulsion composition according to claim 6, wherein the polyhydric alcohol, the lipid and the emulsifier are mixed in amounts of 40-55 wt %, 30-50 wt % and 10-20 wt %, respectively, based on the total weight of the oil phase part.

8. The emulsion composition according to claim 6, wherein the lipid is one or more selected from the group consisting of a phospholipid, a wax, a butter and a ceramide.

9. The emulsion composition according to claim 8, wherein the lipid comprises the phospholipid and the wax, and the phospholipid and the wax are mixed at a weight ratio of 1:9-18.

10. The emulsion composition according to claim 9, wherein the lipid further comprises the ceramide, and the ceramide is mixed with the phospholipid at a weight ratio of 1:3 to 3:1.

11. The emulsion composition according to claim 6, wherein the polyhydric alcohol is one or more selected from the group consisting of butylene glycol, propylene glycol, glycerin, pentylene glycol, dipropylene glycol and diglycerin.

12. A method for preparing the emulsion composition according to claim 1, comprising:
- a step of mixing an aqueous phase comprising water-dispersible non-amphiphilic nanocapsules and an oil phase; and
- a step of forming emulsion particles surrounded by the non-amphiphilic nanocapsules.

* * * * *